United States Patent [19]
Williams

[11] Patent Number: 5,447,253
[45] Date of Patent: Sep. 5, 1995

[54] CONDOM DISPENSER

[76] Inventor: Artis H. Williams, P.O. Box 207, Woodmere, N.Y. 11598

[21] Appl. No.: 267,752

[22] Filed: Jul. 5, 1994

Related U.S. Application Data

[63] Continuation-in-part of Ser. No. 172,228, Dec. 22, 1993, abandoned.

[51] Int. Cl.6 .......................... B65G 59/06; B65H 1/06
[52] U.S. Cl. ...................................... 221/92; 221/191; 221/281; 221/303; 221/312 B; 206/44.12; 220/526
[58] Field of Search ................. 221/281, 92, 191, 194, 221/306, 312 B, 312 C, 303, 312 R; 206/44.11, 44.12; 220/334, 343, 526, 555

[56] References Cited

U.S. PATENT DOCUMENTS

| | | |
|---|---|---|
| 691,990 | 1/1902 | Warren . |
| 1,106,218 | 8/1914 | Homburg . |
| 2,008,875 | 7/1935 | Peterson et al. . |
| 2,211,349 | 8/1940 | Nye . |
| 2,748,677 | 6/1956 | Berlant . |
| 2,815,147 | 12/1957 | Jenkins et al. . |
| 3,620,361 | 11/1971 | Fugiwara . |
| 3,927,809 | 12/1975 | Klein, Sr. . |
| 4,043,485 | 8/1977 | Tippetts ........................ 221/312 R |
| 4,133,421 | 1/1979 | Hanley et al. .............. 221/312 R X |
| 4,170,325 | 10/1979 | Pawlowski . |
| 4,382,526 | 5/1983 | Stone . |
| 4,405,044 | 9/1983 | Flower et al. . |
| 4,491,242 | 1/1985 | Trindad ........................ 221/312 R |
| 4,538,726 | 9/1985 | Pastva ........................ 221/312 C X |
| 4,658,962 | 4/1987 | Burns et al. . |
| 4,759,468 | 7/1988 | Hoffman ............................. 221/20 |
| 4,767,022 | 8/1988 | Oldorf . |
| 4,805,820 | 2/1989 | Kearney . |
| 5,016,661 | 5/1991 | Israel et al. . |
| 5,056,683 | 10/1991 | O'Brien et al. .............. 221/312 R X |
| 5,117,841 | 6/1992 | McBeth . |
| 5,135,135 | 8/1992 | Olivier ........................ 221/303 X |
| 5,176,250 | 1/1993 | Cheng . |

FOREIGN PATENT DOCUMENTS

| | | |
|---|---|---|
| 167465 | 5/1934 | Switzerland . |
| 442835 | 9/1935 | United Kingdom . |
| 456240 | 11/1936 | United Kingdom . |

*Primary Examiner*—William E. Terrell
*Assistant Examiner*—Dean A. Reichard
*Attorney, Agent, or Firm*—Richard C. Litman

[57] ABSTRACT

A dispenser for condoms includes a box-like structure with two side walls, a front wall, a back wall, and a slanting floor. The condoms are loaded through the top of the dispenser and gravity fed through a dispensing slot at the bottom of the dispenser. A second embodiment includes a loading tool which facilitates the orderly loading of packages of condoms within the dispenser. The loading tool includes a loading platform and a detachable handle. The detachable handle is inserted through a vertical slot in the rear of the dispenser and attached to the loading platform disposed within the dispenser. The loading platform is lowered within the dispenser as condoms are stacked on the loading platform.

6 Claims, 4 Drawing Sheets

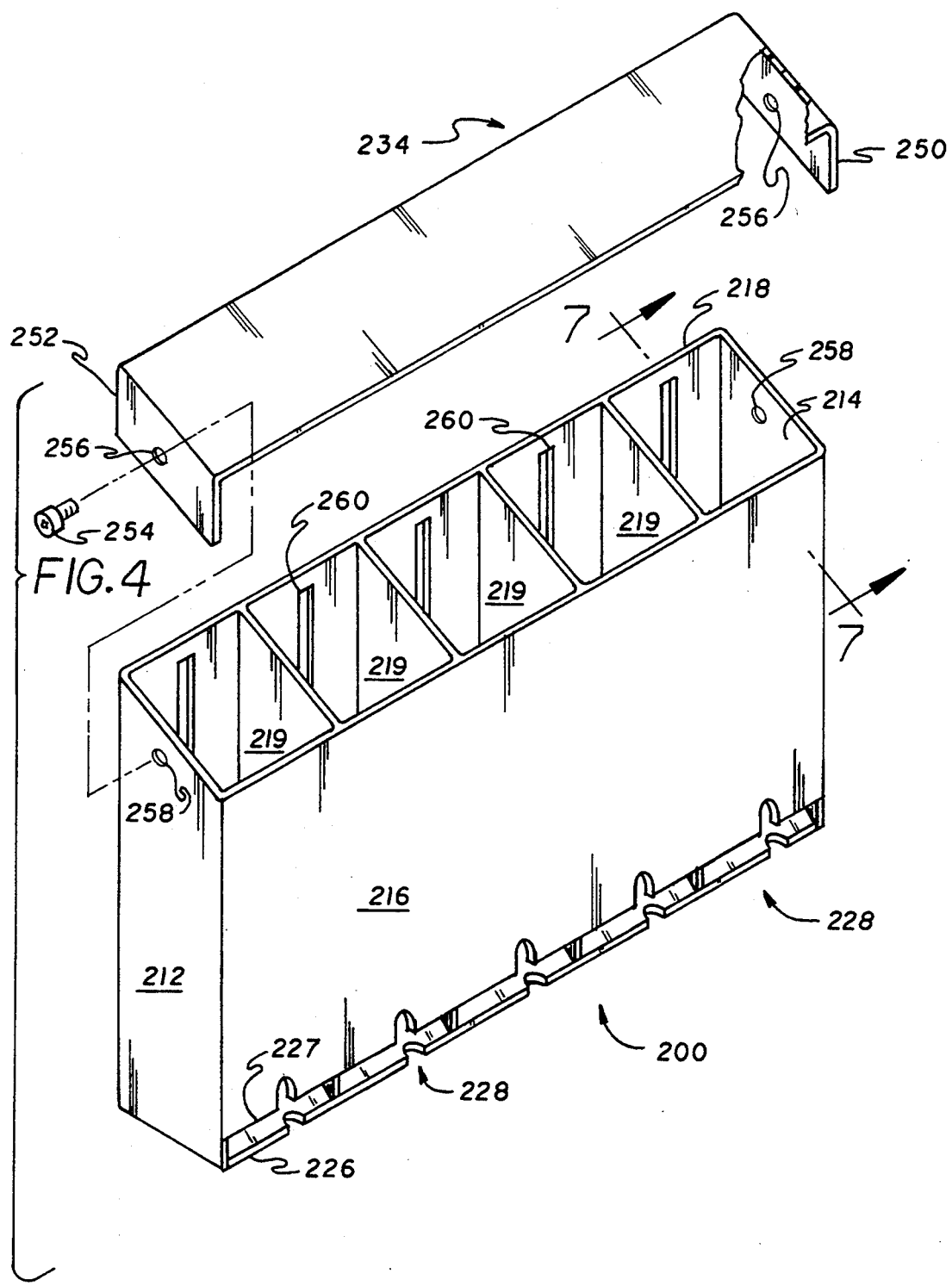

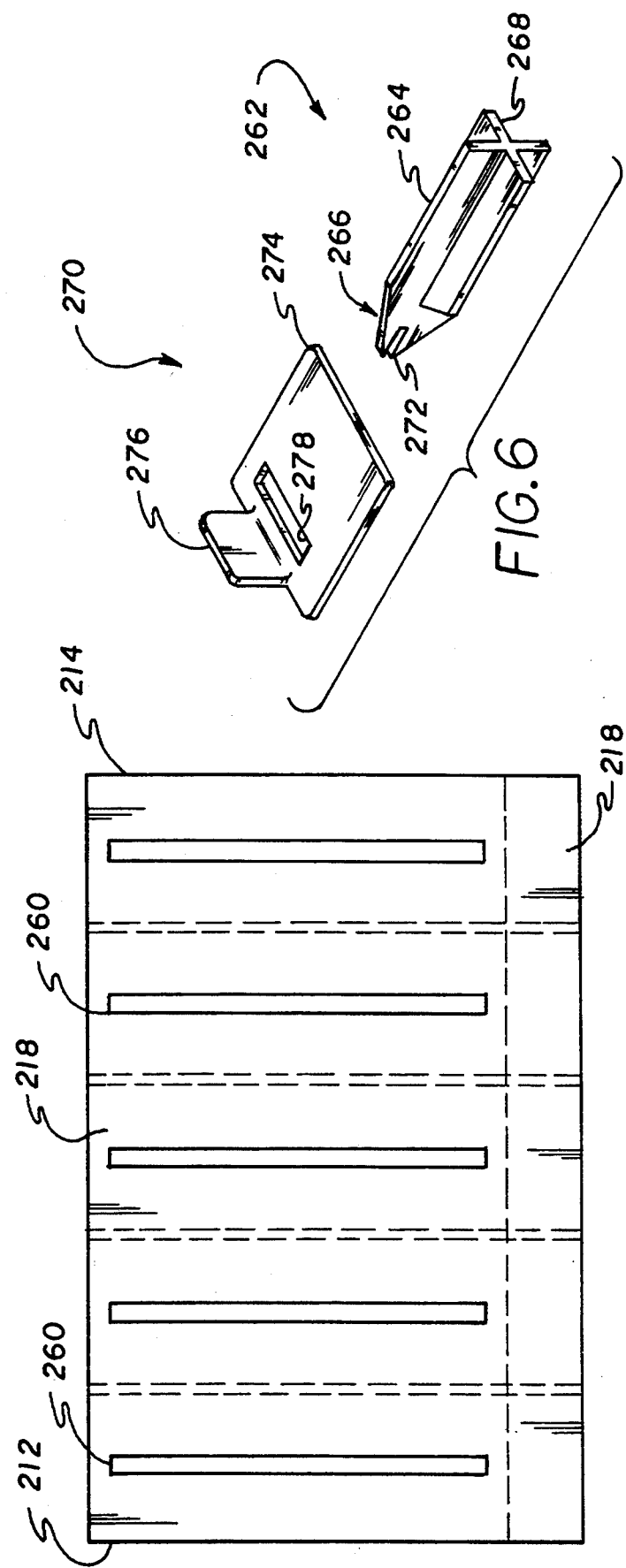

CONDOM DISPENSER

CROSS-REFERENCE TO RELATED APPLICATIONS

This application is a continuation-in-part of application, Ser. No. 08/172,228, filed Dec. 22, 1993, now abandoned.

BACKGROUND OF THE INVENTION

1. Field of the Invention

The present invention relates to an apparatus for storing and dispensing condoms.

2. Description of the Prior Art

The number of AIDS cases today has reached epidemic proportions. With the ever increasing number of AIDS cases and the rising rate of other sexually transmitted diseases, there is a great need for an inexpensive, simple, and discrete means for storing and dispensing free condoms for use by the public. Storage devices for condoms are known in the art. Various inventions provide for the storage of several condoms for individual use. However, none of these devices provide means for storing and dispensing the condoms to the public with the ease and simplicity of the present invention. Packet dispensers are also generally known to the public, but none of the dispensers are designed specifically for condoms, nor do they provide designs which would allow for the quick and simple loading of a number of condoms for use by the public.

U.S. Pat. No. 691,990, issued to Alfred N. Warren on Jan. 28, 1902 discloses a Carton Spice Cabinet which includes a series of vertically arranged compartments, a horizontal base, and a series of rearwardly projecting extensions. Each vertically arranged compartment includes a vertical slot extending along the entire its length and an aperture at the lower ends of the vertically arranged compartments. The cabinet of the '990 patent, however, fails to provide a slanted dispensing floor which facilitates removal of condoms.

U.S. Pat. No. 1,106,218, issued to Alfred J. Homburg on Aug. 4, 1914, discloses a Match Safe comprising a receptacle for receiving matches and a restricted slot that allows only one match to be dispensed at a time. A similar design for a condom dispenser would require that a restricted slot be formed to allow only condoms of a specific size and shape to be dispensed.

U.S. Pat. No. 2,008,875, issued to Thomas H. Peterson et al. on Jul. 7, 1935, discloses a Container for Prophylactic Rubbers comprising an outer casing with separate compartments. The invention allows for storage of condoms but does not provide a convenient means for dispensing the condoms.

U.S. Pat. No. 2,211,349, issued to Earl D. Nye on Aug. 13, 1940, discloses a Bread Dispenser comprising a receptacle like body, an opening through which the articles are introduced, an outlet, and a mechanical ejector for expelling the articles through the outlet. The present invention's design removes the need for a mechanical ejector.

U.S. Pat. No. 2,748,677, issued to Sigmund Berlant on Jun. 5, 1956, discloses a Container For Developing Tanks. The device of the '677 patent includes a container partitioned into compartments for receiving various film developing solutions, but is not designed for the dispensing of condoms or similar objects.

U.S. Pat. No. 3,620,361, issued to Hirotomo Fugiwara on Nov. 16, 1971, discloses a Casing For A Tape Cartridge which includes a rectangular casing with a hinged cover. The cover is hinged to the case body by means of a pair of pins provided at the opposite ends of the cover near one edge thereof within pin holes provided on the case body. The invention of the 361' patent, however, fails to provide a dispensing slot through which condoms may be dispensed.

U.S. Pat. No. 3,927,809, issued to Richard W. Klein, Sr. on Dec. 23, 1975 discloses a Film Cartridge Carrier which includes an inner liner, a cover of flexible material, and a strap. The carrier of the 809' patent, however, fails to provide a slanted bottom wall that facilities the dispensing of condoms.

U.S. Pat. No. 4,170,325 issued to Thomas D. Pawlowski on Oct. 9, 1979 and U.S. Pat. No. 4,405,044, issued to David I. Flower et al. on Sep. 20, 1983 both disclose dispenser boxes which includes a front panel, a corresponding rear panel, a top panel, a corresponding bottom panel, a pair of side panel, and an opening disposed at the bottom of the front panel. The inventions of the '325 patent and the '044 patent, however, fail to provide a dispenser with a hinged top or slanted bottom.

U.S. Pat. No. 4,382,526, issued to Orison W. Stone on May 10, 1983 discloses a wall-mounted paperboard container for dispensing stacked articles which includes a mouth opening in a lower portion of a front wall.

U.S. Pat. No. 4,658,962, issued to Ronald R. Burns et al. on Apr. 21, 1987 discloses a Bag Dispensing Carton comprising a rectangular bottom tray and a rectangular top cover. The invention does not allow convenient loading from the top with a separate opening for dispensing from the bottom.

U.S. Pat. No. 4,767,022, issued to Dennis Oldorf on Aug. 30, 1988, discloses a Packet Dispenser comprising a housing with a plurality of vertically disposed magazines inserted within the housing. The loading of condoms into the Packet Dispenser would require that each magazine be loaded with condoms as opposed to simply loading a single cavity as with the present invention.

U.S. Pat. No. 4,805,820, issued to Thomas G. Kearney on Feb. 21, 1989, discloses a Portable Receptacle comprising a oval shaped casing closed on one end for carrying condoms. The Portable Receptacle provides a means for storing condoms but does not provide a means for dispensing condoms.

U.S. Pat. No. 5,117,841, issued to Charles R. McBeth on Jun. 2, 1992, discloses a Condom Keeper and Kit comprising a receptacle portion with an opening to receive condoms and a cover portion adapted to cover the opening after a condom is received. The Condom Keeper and Kit requires that a plurality of condoms be kept in a separate storage container and then transferred to its receptacle portion. The present invention eliminates this cumbersome arrangement with a simple design which allows storing and dispensing of the condoms.

Swiss Patent Document No. 167,465, published May 16, 1934, discloses a dispenser having a dispenser slot at the bottom end of a front wall, and a floor. The floor has a first slanted section extending from the rear of the dispenser and second slated section extending from the first slanted section to terminate at the dispenser slot.

Other patents, cited by the Examiner in the Office Action associated with the parent application of this continuation-in-part, but not relied upon by the Examiner, include U.S. Pat. No. 2,815,147, issued to Joe H.

Jenkins et al. on Dec. 3, 1957 and U.S. Pat. No. 5,176,250, issued to Billy Cheng on Jan. 5, 1993.

None of the above inventions and patents, taken either singly or in combination, is seen to describe the instant invention as claimed.

SUMMARY OF THE INVENTION

The present invention is a dispenser for condoms which allows condoms to be easily loaded and dispensed. The dispenser accommodates various sizes of condoms and dispenses these condoms without the need for the mechanical parts required by coin operated condom dispensers. The dispenser includes a box-like structure with two side walls, a front wall, a back wall, and a slanting floor. The condoms are loaded through the top of the dispenser and gravity fed through a dispensing slot at the bottom of the dispenser. The slanted floor of the dispenser facilitates removal of condoms from the dispensing slot.

The dispenser may also include a loading tool which facilitates the orderly loading of packages of condoms within the dispenser. The loading tool includes a loading platform and a detachable handle. The detachable handle is inserted through a vertical slot in the rear of the dispenser and attached to the loading platform disposed within the dispenser. The loading platform is lowered within the dispenser as condoms are stacked on the loading platform. Once the dispenser is fully loaded, the handle is detached from the loading platform and the loading platform removed through the dispensing slot.

Accordingly, it is a principal object of the invention to provide a gravity feed condom dispenser.

It is another object of the invention to provide a condom dispenser with a slanted floor to facilitate the removal of condoms from a dispensing slot.

It is a further object of the invention to provide a loading tool for use with the dispenser.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 4 is a front perspective view of a second embodiment of the present invention.

FIG. 5 is a rear elevational view of the second embodiment of the present invention.

FIG. 6 is a perspective view of the loading device use with the dispenser of the second embodiment.

Similar reference characters denote corresponding features consistently throughout the attached drawings.

DETAILED DESCRIPTION OF THE PREFERRED EMBODIMENTS

Figure 3:
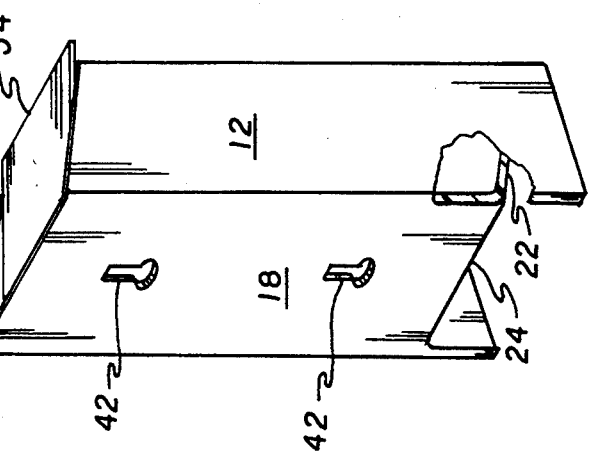
FIG. 3 is a perspective rear view of the dispenser.
Figure 2:
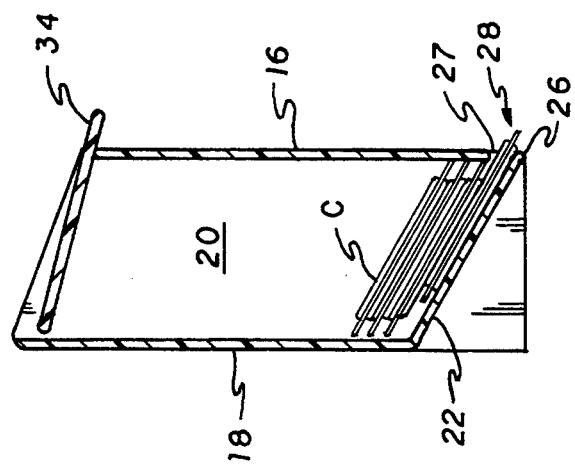
FIG. 2 is an environmental cross-sectional view of FIG. 1 taken along the line 2—2 and showing individually wrapped condoms stacked in the dispenser.
Figure 1:
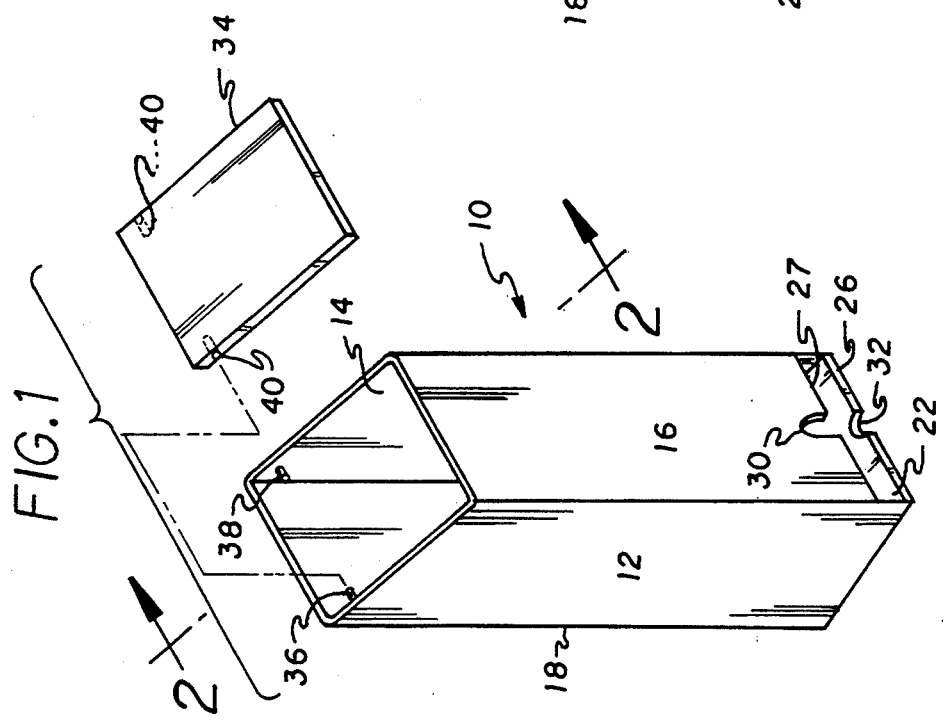
FIG. 1 is an exploded perspective front view of a dispenser of the present invention.

With more detail reference to the drawings, and first to FIG. 1, FIG. 2, and FIG. 3, a condom dispenser 10 of the present invention includes sidewalls 12,14, a front wall 16, and a back wall 18. The sidewalls 12,14, front wall 16, and back wall 18 define a vertical passageway 20 through which wrapped packages of condoms C may descend. A slanted floor 22 extends downwardly from a bottom edge 24 of the back wall 18 to terminate in a front edge 26. The front edge 26 of the slanted floor 22 and the bottom edge 27 of the front wall 16 define a dispensing slot 28 for the condoms C. A stack of individually wrapped condoms C disposed within the vertical passageway 20 and supported by the slanted floor 22 shown in FIG. 2. The slanted floor 22 facilitates the gravity feed of the condoms to the dispensing slot 28, while finger notches 30,32 in the front wall 16 and slanted floor 22 allow the user to grasp and remove a condom from the dispensing slot 28.

As shown in FIG. 1, the dispenser 10 includes a top 34 pivotally connected to the sidewalls 12,14. The sidewalls 12,14 have projections 36,38 which fit into apertures 40 on the side of the top 34, allowing the pivotal mounting of the top 34.

The condom dispenser 10 may be mounted to a vertical structure such as a wall using the mounting holes 42 on the back wall 18 of the dispenser 10. The dispenser 10 may also sit on any horizontal surface, supported by the sidewalls 12,14. In addition, the condom dispenser 10 may be supported in a slightly inclined position by resting the dispenser on a stand or easel structure (not shown). The condom dispenser may also include a vertical slot in the rear wall and a loading device as described below for the second embodiment and illustrated in FIG. 4. In such a case, the mounting holes 42 would be eliminated and replaced by other mounting structure.

The condom dispenser 10 is constructed of plastic or similar material using conventional manufacturing methods. A typical dispenser according to the present invention has a height of approximately seven inches and a width and depth of two and half inches.

A second embodiment of the condom dispenser is shown in FIGS. 4-7. The dispenser 200 of the second embodiment includes sidewalls 212,214, a front wall 216, a back wall 218, and a plurality of compartment walls 219 disposed between the sidewalls 212,214. The compartment walls 219, sidewalls 212,214, front wall 216, and back wall 218 together defining a plurality of vertical passageways 220 (see FIG. 7) through which wrapped packages of condoms may descend. A slanted floor 222 extends downwardly from a bottom edge 224 of the back wall 218 to terminate in a front edge 226. The front edge 226, a bottom edge 227 of said front wall and the compartment walls 219 define a plurality of dispensing slots 228 for the condoms.

As shown in FIG. 4, the dispenser 200 also includes a top cover 234 for preventing access to the vertical passageways 220. The top cover 234 includes flanges 250,252 extending downwardly and disposed adjacent to the sidewalls 212,214. Screws 254 (one shown) are threaded through apertures 256 in the top cover 234 and apertures 258 in the sidewalls 212,214 to secure the top cover 234 to the dispenser 200. Other conventional means may also be used to secure the top cover to the dispenser.

As shown in FIG. 5, the back wall 218 of the dispenser 200 includes a plurality of vertical slots 260 which facilitates the use of a loading tool 262. The loading tool 262, as shown in FIG. 6, includes an elongated handle 264 with a first end 266 and a second end 268. The first end 266 is dimensioned for insertion through one of the vertical slots 260 in the back wall 218. The loading tool 262 also includes a loading platform 270 having a rectangular periphery slightly smaller than the cross-section of the vertical passageways 220. The loading platform 270 is dimensioned to pass through the dispensing slots 228. The first end 266 of the handle 264 includes a slot 272 dimensioned for frictional engagement with an edge 274 of the loading platform 270. The edge 274 of the loading platform is secured and supported in the slot 272 of the handle 264. The loading platform 270 may also be detachably connected to the first end 266 of the handle using other conventional means, such as providing a male portion at the first end of the handle and a mating female portion at the loading platform. The loading platform 270 also includes a tab portion 276 for holding the loading platform 270 within the vertical passageway 220 and a aperture 278 which facilitates pulling the loading platform 270 through one of the dispensing slots 228.

Figure 7:
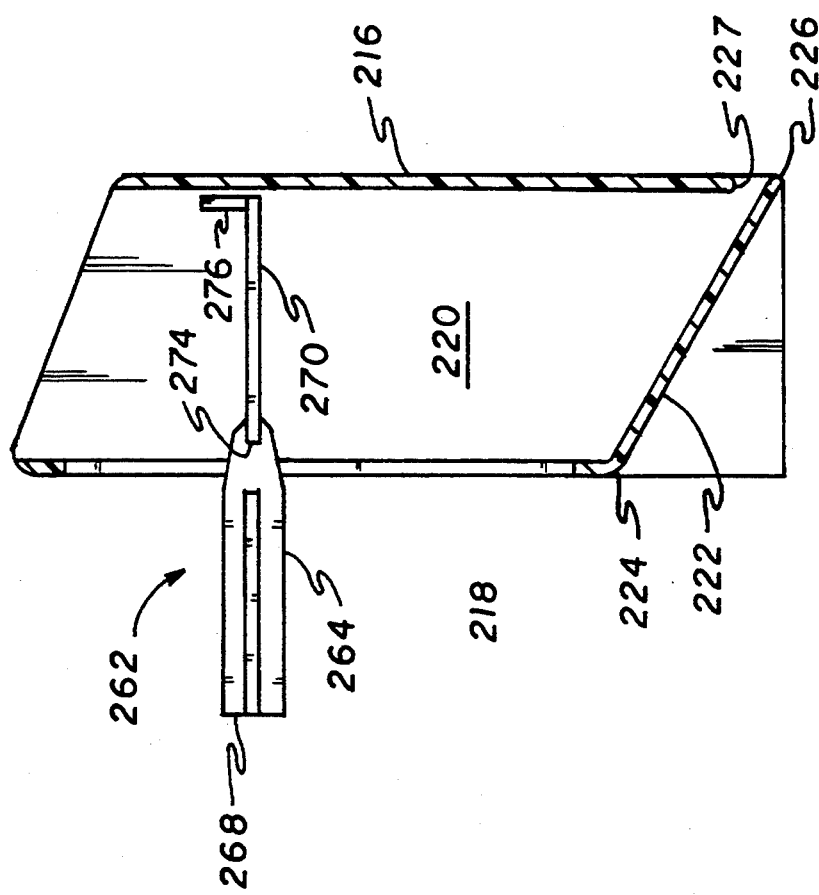
FIG. 7 is a sectional side elevational view taken along line 7—7 of FIG. 4, showing the loading device assembled and disposed within one of the vertical slots of the dispenser.

The loading tool 262 facilities the orderly loading of condoms into the dispenser. In use, the first end 266 of the handle 264 is inserted through one of the vertical slots 260 while the loading platform 270 is held within a vertical passageway 220. The first end 266 of the handle 264 is then secured to the edge 274 of the loading platform 270 as shown in FIG. 7, allowing the user to hold the second end 268 of the handle 264 as condoms are stacked on the loading platform 270. The user lowers the loading tool 262 as condoms are stacked on the platform 270. Once the vertical passageway 220 has been filled with condoms, the handle 264 is disconnected from the platform 270, allowing the loading platform 270 to be pulled through the dispensing slot 228 and removed from the dispenser 200.

The dispenser 200 of the second embodiment may be mounted on a wall or otherwise supported as described for the dispenser 10 of the first embodiment.

It is to be understood that the present invention is not limited to the embodiments described above, but encompasses any and all embodiments within the scope of the following claims.

What is claimed is:

1. A box-like dispenser adapted for vertical disposition and used to dispense individually wrapped condoms, said dispenser comprising:
   a first sidewall;
   a second sidewall;
   a front wall extending from said first sidewall to said second sidewall, said front wall having a top edge and a bottom edge;
   a back wall extending from said first sidewall to said second sidewall, said back wall having a top edge and a bottom edge;
   a vertical slot in said back wall;
   said first sidewall, said second sidewall, said front wall, and said back wall defining a vertical passageway through which condoms may descend;
   a slanted floor extending downwardly from said bottom edge of said back wall to terminate in a front edge, said front edge of said slanted floor and said bottom edge of said front wall defining a dispensing slot for the condoms;
   a top pivotally connected to said first sidewall and to said second sidewall, whereby said top is movable from a closed position to an open position providing access to said vertical passageway; and
   a loading tool having
      an elongated handle with a first end and a second end, said first end dimensioned for insertion through said vertical slot of said back wall,
      a loading platform member having a periphery slightly smaller than the cross-section of said vertical passageway, said loading platform member dimensioned to pass through said dispensing slot, and
      means for detachable connection of said first end of said elongated handle to an edge of said loading platform member,
      whereby said first end is inserted through said vertical slot and attached to said edge of said loading platform member, said loading platform member horizontally disposed within said vertical passageway.

2. The box-like dispenser of claim 1, wherein said bottom edge of said front wall includes a front finger notch, and said front edge of said slanted floor includes a floor finger notch to facilitate grasping a condom disposed in said dispensing slot.

3. The box-like dispenser of claim 2, including a plurality of compartment walls disposed between said first sidewall and said second sidewall, said plurality of compartment walls, said front wall, and said back wall together defining a plurality of vertical passageways.

4. The box-like dispenser of claim 3, including a plurality of vertical slots in said back wall.

5. The box-like dispenser of claim 1, further comprising, in combination, a plurality of individually wrapped condoms stacked within said vertical passageway and supported by said slanted floor.

6. A box-like dispenser adapted for vertical disposition and used to dispense individually wrapped condoms, said dispenser comprising:
   a first sidewall;
   a second sidewall;
   a front wall extending from said first sidewall to said second sidewall, said front wall having a top edge and a bottom edge;
   a back wall extending from said first sidewall to said second sidewall, said back wall having a top edge and a bottom edge;
   a plurality of compartment walls disposed between said first sidewall and said second sidewall, said plurality of compartment walls, said front wall, and said back wall together defining a plurality of vertical passageways through which the condoms may descend;
   a slanted floor extending downwardly from said bottom edge of said back wall to terminate in a front edge, said front edge of said slanted floor, said bottom edge of said front wall, and said plurality of compartment walls defining a plurality of dispensing slots for the condoms;
   a plurality of vertical slots in said back wall; and
   a loading tool having
      an elongated handle with a first end and a second end, said first end dimensioned for insertion through one of said plurality of vertical slots in said back wall, a loading platform member having a rectangular periphery slightly smaller than the cross-section of one of said plurality of vertical passageways, said loading platform member dimensioned to pass through one of said plurality of dispensing slots, and means for detachable connection of said first end of said elongated handle to an edge of said loading platform member, whereby said first end is inserted through one of said plurality of vertical slots and attached to an edge of said loading platform member, with said loading platform member horizontally disposed within one of said plurality of vertical passageways; and a top cover for preventing access to said plurality of vertical passageways, said top cover having a first end and a second end, said first end of said top cover having a first flange extending downwardly and disposed adjacent to said first sidewall, said second end of said top cover having a second flange extending downwardly and disposed adjacent to said second sidewall, and means for securing said first flange and said second flange to said first sidewall and said second sidewall.

* * * * *